(12) United States Patent
Gesing et al.

(10) Patent No.: US 6,887,831 B1
(45) Date of Patent: May 3, 2005

(54) SUBSTITUTED THIENYL(AMINO) SULFONYLUREAS

(75) Inventors: Ernst Rudolf F. Gesing, Erkrath (DE); Joachim Kluth, Langenfeld (DE); Klaus-Helmut Müller, Düsseldorf (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/049,747

(22) PCT Filed: Jul. 25, 2000

(86) PCT No.: PCT/EP00/07096

§ 371 (c)(1),
(2), (4) Date: Jan. 31, 2002

(87) PCT Pub. No.: WO01/10863

PCT Pub. Date: Feb. 15, 2001

(30) Foreign Application Priority Data

Aug. 6, 1999 (DE) .......................... 199 37 118

(51) Int. Cl.⁷ .................. A01N 43/54; A01N 43/66; C07D 409/12
(52) U.S. Cl. .................. 504/230; 544/198; 544/207; 544/209; 544/212
(58) Field of Search .................. 504/230; 544/198, 544/207, 209, 212

(56) References Cited

U.S. PATENT DOCUMENTS

| 4,481,029 A | 11/1984 | Levitt ............................ 71/93 |
| 4,549,898 A | 10/1985 | Böhner et al. ................. 71/90 |
| 4,659,361 A | 4/1987 | Brown ........................... 71/90 |
| 4,668,281 A | 5/1987 | Levitt ............................ 71/93 |
| 4,690,707 A | 9/1987 | Föry et al. ..................... 71/93 |
| 4,701,535 A | 10/1987 | Levitt ........................... 549/60 |
| 4,741,757 A | 5/1988 | Levitt ............................ 71/90 |
| 4,743,290 A | 5/1988 | Christensen et al. ........... 71/90 |
| 4,877,440 A | 10/1989 | Christensen et al. ........... 71/90 |

FOREIGN PATENT DOCUMENTS

| DE | 195 01 174 | 7/1996 |
| EP | 0 030 142 | 6/1981 |
| EP | 0 097 122 | 12/1983 |

OTHER PUBLICATIONS

Aust. J. Chem. (month unavailable) 1995, 48, pp. 1907–1916, Scott A. Henderson, Jacqueline.
O'Connor, Alan R. Rendina, G. Paul Savage and Gregory W. Simpson, The Synthesis and Biological Activity of 'Crippled Biotin'.

*Primary Examiner*—Richard L. Raymond
(74) *Attorney, Agent, or Firm*—Richard E. L. Henderson; Raymond J. Harmuth

(57) ABSTRACT

The invention relates to novel substituted thienyl(amino) sulphonylureas of the general formula (I)

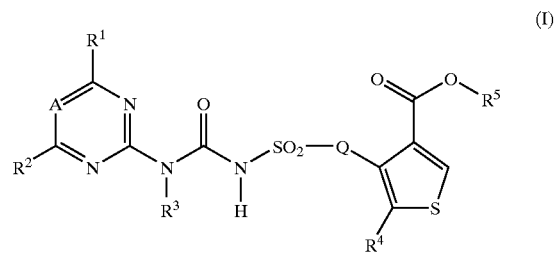

in which A, Q, $R^1$, $R^2$, $R^3$, $R^4$ and $R^5$ are each as defined in the description, to processes for their preparation and to their use as herbicides.

7 Claims, No Drawings

SUBSTITUTED THIENYL(AMINO) SULFONYLUREAS

The present application is a 35 U.S.C. Section 371 national stage of PCT/EP00/07096 filed Jul. 25, 2000.

The invention relates to novel substituted thienyl(amino) sulphonylureas, to processes for their preparation and to their use as herbicides.

It is already known that certain substituted thienylsulphonylureas have herbicidal properties (cf. EP-A-30142/U.S. Pat. No. 4,481,029/U.S. Pat. No. 4,599,103/U.S. Pat. Pat. 4,701,535, EP-A-97122/U.S. Pat. No. 4,549,898, EP-A-207609/U.S. Pat. No. 4,668,281). However, the herbicidal activity of these known compounds is not entirely satisfactory.

This invention, accordingly, provides the novel substituted thienyl(amino)sulphonylureas of the general formula (I)

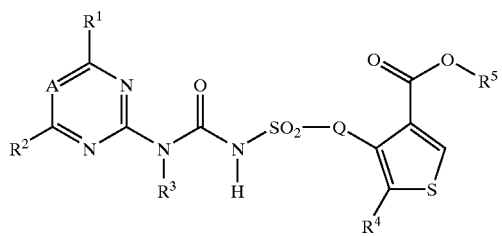

in which
A represents nitrogen or a CH grouping,
Q represents a single bond or represents NH,
$R^1$ represents hydrogen, halogen or in each case optionally substituted alkyl, alkoxy, alkylthio, alkylamino, dialkylamino, aryloxy or heterocyclyloxy,
$R^2$ represents hydrogen, halogen or in each case optionally substituted alkyl, alkoxy, alkylthio, alkylamino, dialkylamino, aryloxy or heterocyclyloxy,
$R^3$ represents hydrogen or optionally substituted alkyl,
$R^4$ represents halogen or optionally substituted alkyl and—if Q represents NH—also represents hydrogen, and
$R^5$ represents hydrogen or in each case optionally substituted alkyl, alkenyl, alkinyl, cycloalkyl, cycloalkylalkyl or heterocyclyl,
and salts of compounds of the formula (I).

Saturated or unsaturated hydrocarbon groupings, such as alkyl, alkenyl or alkinyl, are in each case straight-chain or branched as far as this is possible—including in combination with hetero atoms, such as in alkoxy.

Optionally substituted radicals can be mono- or polysubstituted, where in the case of polysubstitution the substituents can be identical or different.

Preferred substituents or ranges of the radicals which are present in the formulae given above and below are defined below.

A preferably represents nitrogen or a CH grouping.

Q preferably represents a single bond or represents NH.

$R^1$ preferably represents hydrogen, represents halogen, represents in each case optionally cyano-, halogen- or $C_1$–$C_4$-alkoxy-substituted alkyl, alkoxy, alkylthio, alkylamino or dialkylamino having in each case 1 to 4 carbon atoms in the alkyl groups, or represents in each case optionally cyano-, halogen-, $C_1$–$C_4$-alkyl- or $C_1$–$C_4$-alkoxy-substituted phenoxy, oxetanyloxy, furyloxy or tetrahydrofuryloxy.

$R^2$ preferably represents hydrogen, represents halogen, represents in each case optionally cyano-, halogen- or $C_1$–$C_4$-alkoxy-substituted alkyl, alkoxy, alkylthio, alkylamino or dialkylamino having in each case 1 to 4 carbon atoms in the alkyl groups, or represents in each case optionally cyano-, halogen-, $C_1$–$C_4$-alkyl- or $C_1$–$C_4$-alkoxy-substituted phenoxy, oxetanyloxy, furyloxy or tetrahydrofuryloxy.

$R^3$ preferably represents hydrogen or represents optionally $C_1$–$C_4$-alkoxy-, $C_1$–$C_4$-alkyl-carbonyl- or $C_1$–$C_4$-alkoxy-carbonyl-substituted alkyl having 1 to 4 carbon atoms.

$R^4$ preferably represents optionally cyano-, halogen- or $C_1$–$C_4$-alkoxy-substituted alkyl having 1 to 6 carbon atoms and—if Q represents NH—also represents hydrogen.

$R^5$ preferably represents hydrogen, represents optionally cyano-, halogen- or $C_1$–$C_4$-alkoxy-substituted alkyl having 1 to 6 carbon atoms, represents in each case optionally halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety, or represents in each case optionally cyano-, halogen-, $C_1$–$C_4$-alkyl- or $C_1$–$C_4$-alkoxy-substituted oxetanyl, furyl or tetrahydrofuryl.

A particularly preferably represents nitrogen or a CH grouping.

Q particularly preferably represents a single bond or represents NH.

$R^1$ particularly preferably represents hydrogen, fluorine, chlorine, bromine, iodine, or represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino.

$R^2$ particularly preferably represents fluorine, chlorine, bromine, or represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino.

$R^3$ particularly preferably represents hydrogen or represents in each case optionally methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl or ethyl.

$R^4$ particularly preferably represents in each case optionally cyano-, fluorine-, chlorine-, methoxy- or ethoxy-substituted methyl, ethyl, n- or i-propyl, n-, i-, s- or t-butyl.

$R^5$ particularly preferably represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, represents in each case optionally fluorine-, chlorine- or bromine-substituted propenyl, butenyl, propinyl or butinyl, or represents in each case optionally cyano-, fluorine-, chlorine-, bromine-, methyl-, ethyl-, n- or i-propylsubstituted cyclopropyl, cyclobutyl, cyclopentyl, cyclohexyl, cyclopropylmethyl, cyclobutylmethyl, cyclopentylmethyl or cyclohexylmethyl.

A very particularly preferably represents nitrogen or a CH grouping.

Q very particularly preferably represents a single bond or represents NH.

$R^1$ very particularly preferably represents hydrogen, fluorine, chlorine, bromine , represents in each case optionally fluorine-, chlorine-, methoxy- or ethoxy-substituted methyl, ethyl, methoxy, ethoxy, methylthio, ethylthio, methylamino, ethylamino, or represents dimethylamino.

$R^2$ very particularly preferably represents fluorine, chlorine, bromine, represents methyl, ethyl, methoxy, ethoxy, methylthio, ethylthio, methylamino or ethylamino, or represents dimethylamino.

$R^3$ very particularly preferably represents hydrogen or methyl.

$R^4$ very particularly preferably represents in each case optionally fluorine- or chlorine-substituted methyl, ethyl, n- or i-propyl.

$R^5$ very particularly preferably represents in each case optionally fluorine-, chlorine-, methoxy- or ethoxy-substituted methyl, ethyl, n- or i-propyl, or represents in each case optionally fluorine- or chlorine-substituted propenyl or propinyl.

A most preferably represents a CH grouping.

$R^1$ and $R^2$ most preferably represent methoxy.

$R^3$ most preferably represents hydrogen.

The invention also preferably provides the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium- and di-($C_1$–$C_2$-alkyl)-benzyl-ammonium salts of compounds of the formula (I), in which A, Q, $R^1$, $R^2$, $R^3$, $R^4$ and $R^5$ have the meaning given above as being preferred.

The abovementioned general or preferred radical definitions apply both to the end products of the formula (I) and, correspondingly, to the starting materials or intermediates required in each case for the preparation. These radical definitions can be combined with one another as desired, i.e. including combinations between the given ranges of preferred compounds.

Preference according to the invention is given to those compounds of the formula (I) which contain a combination of the meanings given above as being preferred.

Particular preference according to the invention is given to those compounds of the formula (I) which contain a combination of the meanings given above as being particularly preferred.

Very particular preference according to the invention is given to those compounds of the formula (I) which contain a combination of the meanings given above as being very particularly preferred.

Most preference according to the invention is given to the compounds in which $R^1$, $R^2$, $R^3$ or A have one of the meanings given as being most preferred.

Examples of the compounds of the formula (I) according to the invention are listed in the groups below.

Group 1

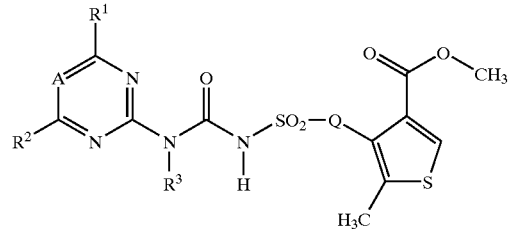

(IA-1)

Here, A, Q, $R^1$, $R^2$ and $R^3$ have, for example, the meanings listed below:

| A | Q | $R^1$ | $R^2$ | $R^3$ |
|---|---|---|---|---|
| CH | — | $OCH_3$ | $OCH_3$ | H |
| CH | NH | $OCH_3$ | $OCH_3$ | H |
| CH | — | $CH_3$ | $OCH_3$ | H |
| CH | NH | $CH_3$ | $OCH_3$ | H |
| CH | — | $CH_3$ | $CH_3$ | H |
| CH | NH | $CH_3$ | $CH_3$ | H |
| CH | — | Cl | $OCH_3$ | H |
| CH | — | H | $CH_3$ | H |
| N | — | $CH_3$ | $OCH_3$ | $CH_3$ |
| N | — | $OCH_3$ | $OCH_3$ | $CH_3$ |
| N | — | $CH_3$ | $OCH_3$ | H |
| N | NH | $CH_3$ | $OCH_3$ | H |
| N | — | $OCH_3$ | $OCH_3$ | H |
| N | NH | $OCH_3$ | $OCH_3$ | H |
| N | — | $CH_3$ | $CH_3$ | H |
| N | — | $OCHF_2$ | $N(CH_3)_2$ | H |
| N | — | $CH_3$ | $SCH_3$ | H |
| N | — | $C_2H_5$ | $OCH_3$ | H |
| N | — | $CH_3$ | $OC_2H_5$ | H |
| N | — | H | $OCH_3$ | H |
| N | — | $OCH_3$ | cyclopropyl | H |
| N | — | $CH_3$ | $N(CH_3)_2$ | H |
| CH | — | $OCH_3$ | oxetanyloxy | H |
| CH | — | $CH_3$ | oxetanyloxy | H |
| CH | — | Cl | oxetanyloxy | H |
| N | — | H | oxetanyloxy | H |
| N | — | $N(CH_3)_2$ | $OCH_2CF_3$ | H |

Group 2

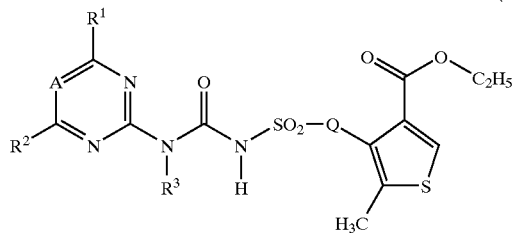
(IA-2)

Here, A, Q, $R^1$, $R^2$ and $R^3$ have, for example, the meaning given above in Group 1.

Group 3

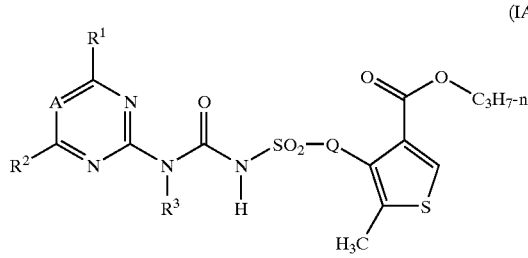
(IA-3)

Here, A, Q, $R^1$, $R^2$ and $R^3$ have, for example, the meaning given above in Group 1.

Group 4

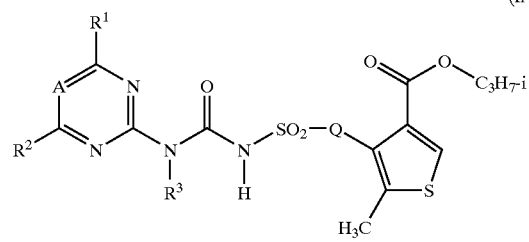
(IA-4)

Here, A, Q, $R^1$, $R^2$ and $R^3$ have, for example, the meaning given above in Group 1.

Group 5

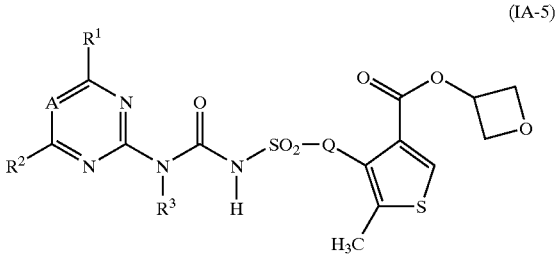
(IA-5)

Here, A, Q, $R^1$, $R^2$ and $R^3$ have, for example, the meaning given above in Group 1.

Group 6

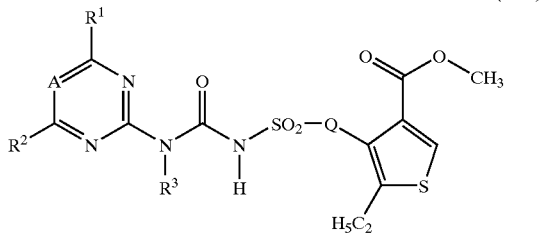
(IA-6)

Here, A, Q, $R^1$, $R^2$ and $R^3$ have, for example, the meaning given above in Group 1.

Group 7

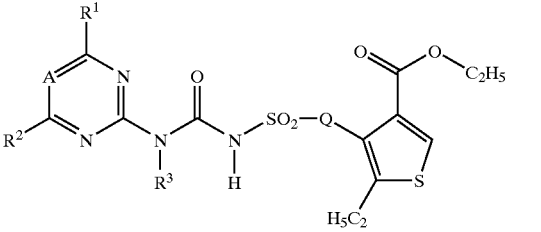
(IA-7)

Here, A, Q, $R^1$, $R^2$ and $R^3$ have, for example, the meaning given above in Group 1.

Group 8

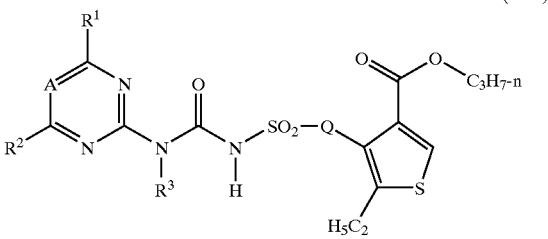
(IA-8)

Here, A, Q, $R^1$, $R^2$ and $R^3$ have, for example, the meaning given above in Group 1.

Group 9

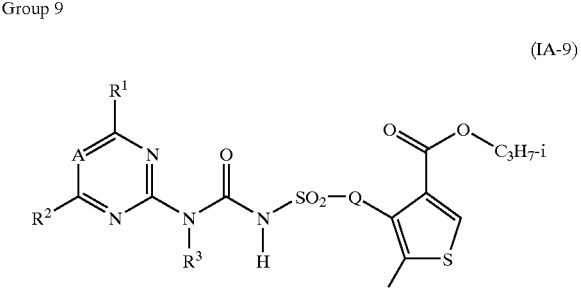
(IA-9)

Here, A, Q, $R^1$, $R^2$ and $R^3$ have, for example, the meaning given above in Group 1.

Group 10

(IA-10)

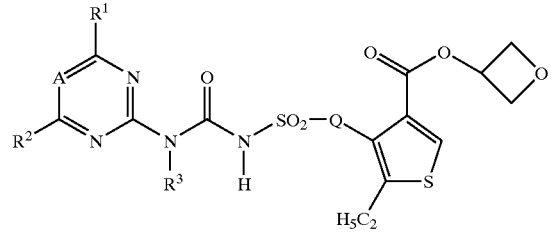

Here, A, Q, $R^1$, $R^2$ and $R^3$ have, for example, the meaning given above in Group 1.

Group 11

(IA-11)

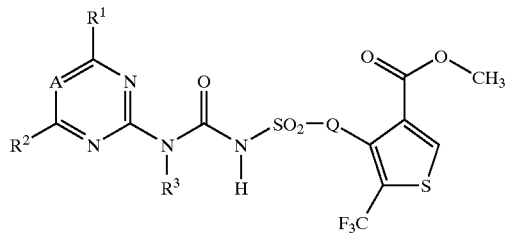

Here, A, Q, $R^1$, $R^2$ and $R^3$ have, for example, the meaning given above in Group 1.

Group 12

(IA-12)

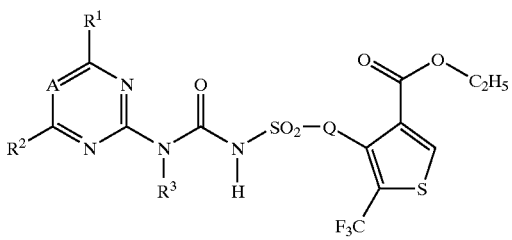

Here, A, Q, $R^1$, $R^2$ and $R^3$ have, for example, the meaning given above in Group 1.

Group 13

(IA-13)

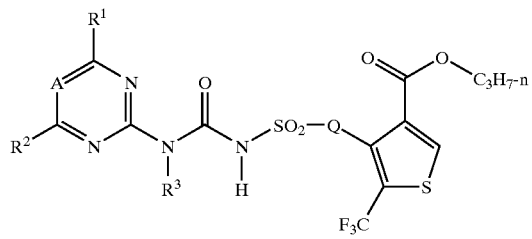

Here, A, Q, $R^1$, $R^2$ and $R^3$ have, for example, the meaning given above in Group 1.

Group 14

(IA-14)

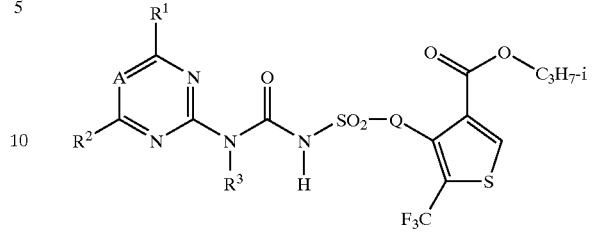

Here, A, Q, $R^1$, $R^2$ and $R^3$ have, for example, the meaning given above in Group 1.

Group 15

(IA-15)

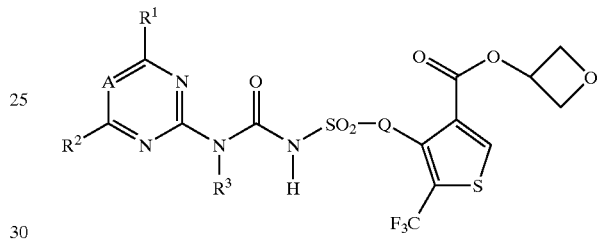

Here, A, Q, $R^1$, $R^2$ and $R^3$ have, for example, the meaning given above in Group 1.

Group 16

(IA-16)

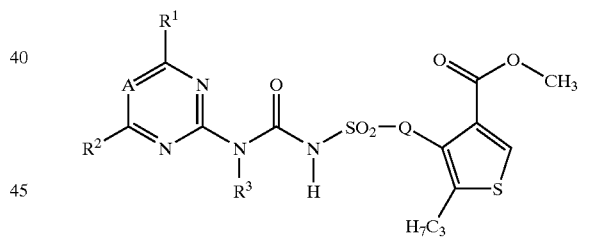

Here, A, Q, $R^1$, $R^2$ and $R^3$ have, for example, the meaning given above in Group 1.

Group 17

(IA-17)

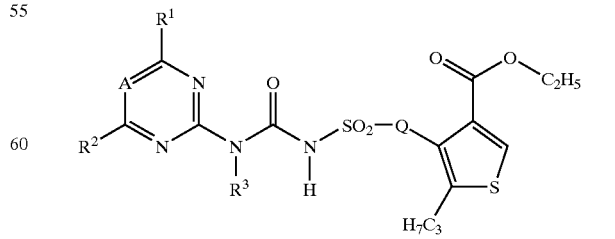

Here, A, Q, $R^1$, $R^2$ and $R^3$ have, for example, the meaning given above in Group 1.

Group 18

(IA-18)

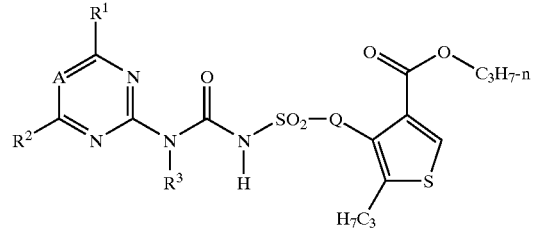

Here, A, Q, R$^1$, R$^2$ and R$^3$ have, for example, the meaning given above in Group 1.

Group 19

(IA-19)

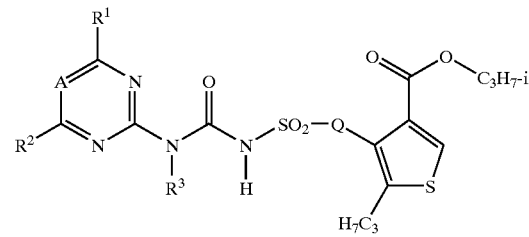

Here, A, Q, R$^1$, R$^2$ and R$^3$ have, for example, the meaning given above in Group 1.

Group 20

(IA-20)

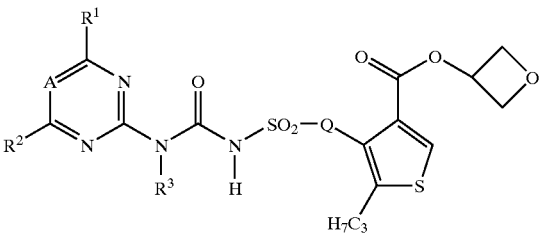

Here, A, Q, R$^1$, R$^2$ and R$^3$ have, for example, the meaning given above in Group 1.

Group 21

(IA-21)

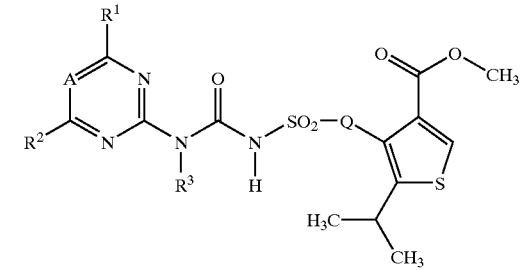

Here, A, Q, R$^1$, R$^2$ and R$^3$ have, for example, the meaning given above in Group 1.

Group 22

(IA-22)

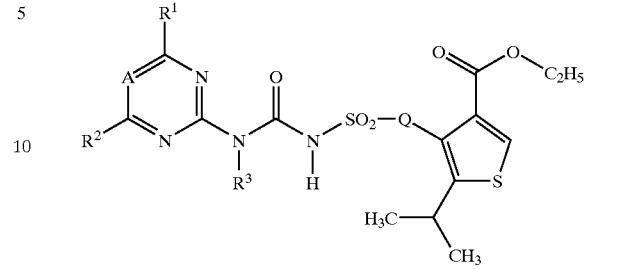

Here, A, Q, R$^1$, R$^2$ and R$^3$ have, for example, the meaning given above in Group 1.

Group 23

(IA-23)

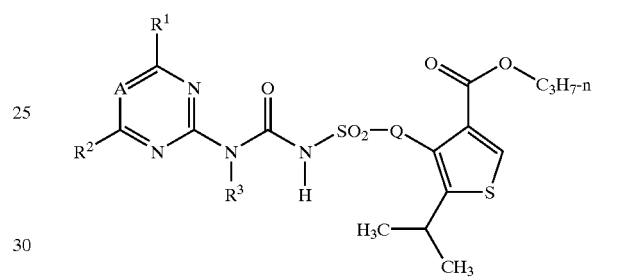

Here, A, Q, R$^1$, R$^2$ and R$^3$ have, for example, the meaning given above in Group 1.

Group 24

(IA-24)

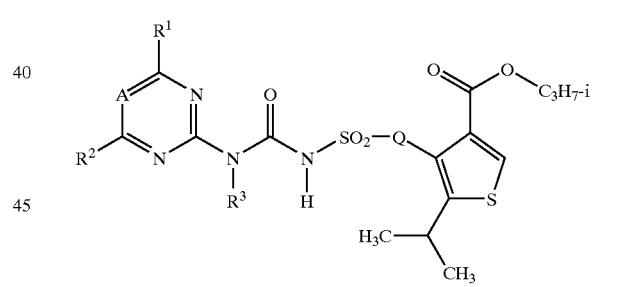

Here, A, Q, R$^1$, R$^2$ and R$^3$ have, for example, the meaning given above in Group 1.

Group 25

(IA-25)

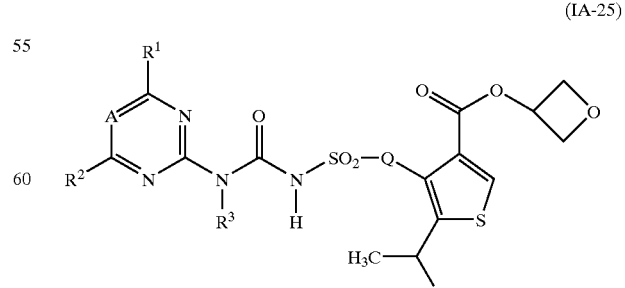

Here, A, Q, R$^1$, R$^2$ and R$^3$ have, for example, the meaning given above in Group 1.

The novel substituted thienyl(amino)sulphonylureas of the general formula (I) have strong herbicidal activity.

The novel substituted thienyl(amino)sulphonylureas of the general formula (I) are obtained when (a) aminoazines of the general formula (II)

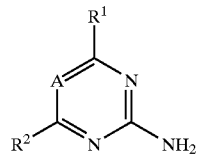
(II)

in which
A, $R^1$ and $R^2$ are each as defined above
are reacted with thienyl(amino)sulphonyl isocyanates of the general formula (E)

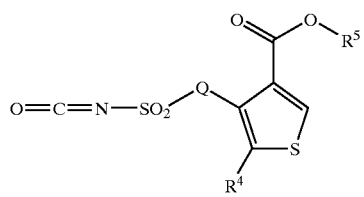
(III)

in which
Q, $R^4$ and $R^5$ are each as defined above,
if appropriate in the presence of a reaction auxiliary and if appropriate in the presence of a diluent,
or when (b) substituted aminoazines of the general formula (IV)

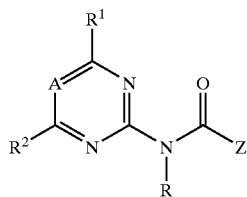
(IV)

in which
A, $R^1$ and $R^2$ are each as defined above,
Z represents halogen, alkoxy or aryloxy and
R has the meaning given above for $R^3$ or represents the grouping —C(O)—Z,
are reacted with thiophene derivatives of the general formula (V)

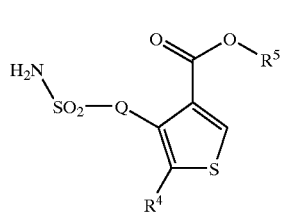
(V)

in which
Q, $R^4$ and $R^5$ are each as defined above, if appropriate in the presence of a reaction auxiliary and if appropriate in the presence of a diluent,
or when (c) aminoazines of the general formula (II)

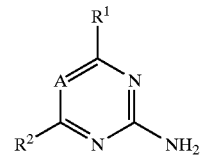
(II)

in which
A, $R^1$ and $R^2$ are each as defined above,
are reacted with thiophene derivatives of the general formula (VI)

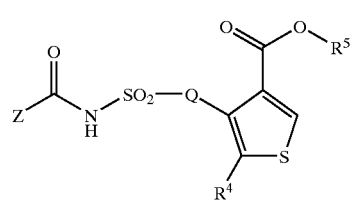
(VI)

in which
Q, $R^4$ and $R^5$ are each as defined above and
Z represents halogen, alkoxy or aryloxy,
if appropriate in the presence of a reaction auxiliary and if appropriate in the presence of a diluent,
or when (d) aminoazines of the general formula (II)

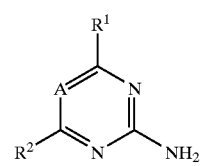
(II)

in which
A, $R^1$ and $R^2$ are each as defined above,
are reacted with chlorosulphonyl isocyanate, if appropriate in the presence of a diluent, and the resulting chlorosulphonylaminocarbonylamino-azines of the general formula (VII)

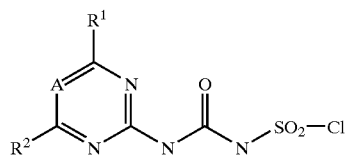
(VII)

in which
A, $R^1$ and $R^2$ are each as defined above
are—after intermediate isolation or "in situ"-
reacted with substituted aminothiophenes of the general formula (VII)

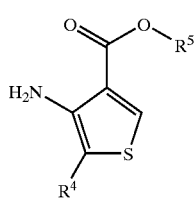

(VIII)

in which

R⁴ and R⁵ are each as defined above, if appropriate in the presence of a reaction auxiliary and if appropriate in the presence of a diluent, and the compounds of the formula (I) obtained by process (a), (b), (c) or (d) are, if appropriate, converted by customary methods into salts.

Using, for example, 2-amino-4-methoxy-6-methyl-pyrimidine and 4-ethoxycarbonyl-2-trifluoromethyl-thien-3-yl-sulphonyl isocyanate as starting materials, the course of the reaction in the process (a) according to the invention can be illustrated by the following formula scheme:

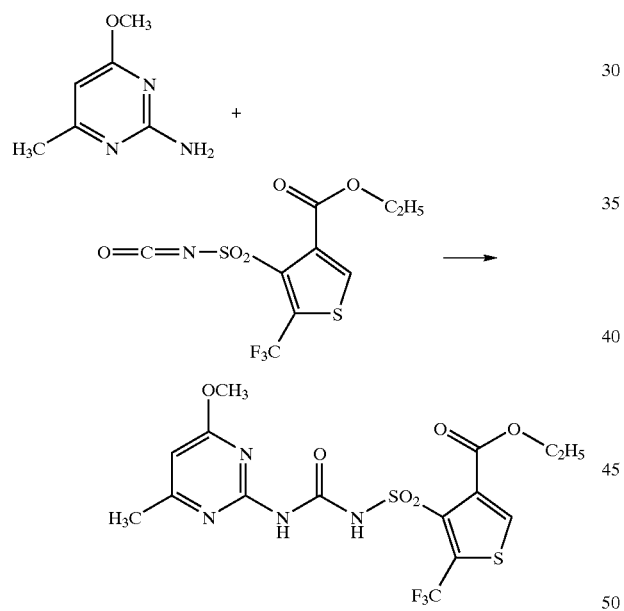

Using, for example, 2-methoxycarbonylamino 4-methoxy-6-trifluoromethyl-1,3,5-triazine and 2-ethyl-4-i-propoxycarbonyl-thiophene-3-sulphonamide as starting materials, the course of the reaction in the process (b) according to the invention can be illustrated by the following formula scheme:

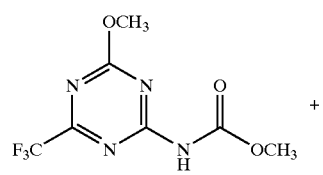

Using, for example, 2-amino-4-chloro-6-methoxy-pyrimidine and O-phenyl N-(4-ethoxycarbonyl-2-methyl-thien-3-yl-sulphonyl)-urethane as starting materials, the course of the reaction in the process (c) according to the invention can be illustrated by the following formula scheme:

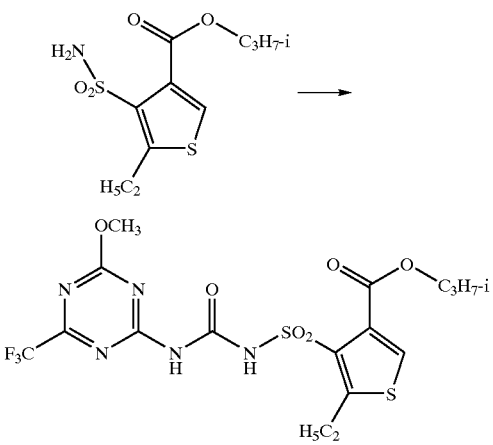

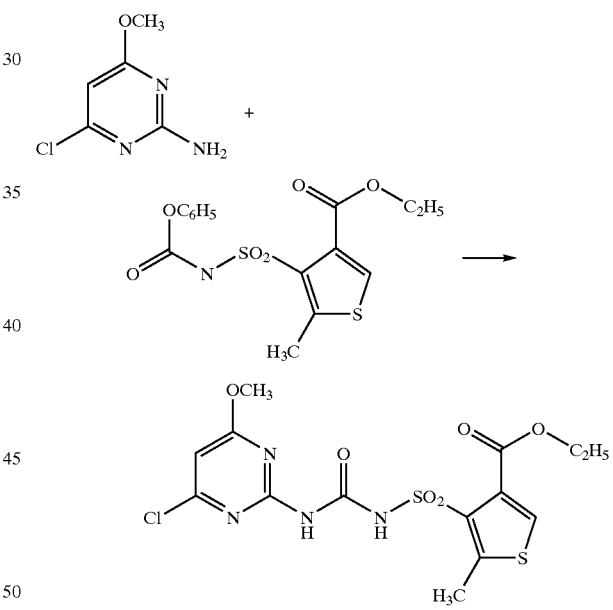

Using, for example, 2-amino-4-methoxy-6-trifluoromethyl-pyrimidine, chlorosulphonyl isocyanate and ethyl 3-amino-2-ethyl-thiophene-4-carboxylate as starting materials, the course of the reaction in the process (d) according to the invention can be illustrated by the following formula scheme:

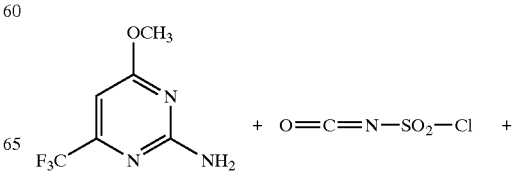

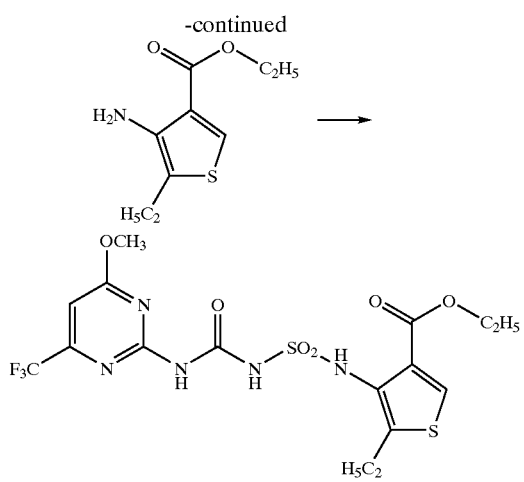

The formula (II) provides a general definition of the aminoazines to be used as starting materials in the processes (a), (c) and (d) according to the invention for preparing the compounds of the general formula (I). In the formula (II), A, $R^1$ and $R^2$ each preferably or in particular have those meanings which have already been mentioned above, in connection with the description of the compounds of the formula (I), as being preferred or as being particularly preferred for A, $R^1$ and $R^2$.

The aminoazines of the formula (II) are known chemicals for synthesis, some of which are commercially available.

The formula (III) provides a general definition of the thienyl(amino)sulfonyl isocyanates further to be used as starting materials in the process (a) according to the invention. In the formula (III), Q, $R^4$ and $R^5$ each preferably or in particular have those meanings which have already been mentioned above, in connection with the description of the compounds of the formula (I), as being preferred or as being particularly preferred for Q, $R^4$ and $R^5$.

The starting materials of the formula (III) are known and/or can be prepared by processes known per se (cf. EP 30142/U.S. Pat. No. 4,481,029/U.S. Pat. No. 4,599,103/U.S. Pat. No. 4,701,535).

The thienyl(amino)sulphonyl isocyanates of the formula (d) are obtained when thiophene derivatives of the general formula (V)—above—are reacted with phosgene or thiophosgene, if appropriate in the presence of an alkyl isocyanate, such as, for example, butyl isocyanate, if appropriate in the presence of a reaction auxiliary, such as, for example, diazabicyclo[2.2.2]octane, and in the presence of a diluent, such as, for example, toluene, xylene or chlorobenzene, at temperatures between 80° C. and 150° C., and the volatile components are, after the reaction has ended, distilled off under reduced pressure.

The formula (IV) provides a general definition of the substituted aminoazines to be used as starting materials in the process (b) according to the invention for preparing the compounds of the formula (I). In the formula (IV), A, $R^1$ and $R^2$ each preferably or in particular have those meanings which have already been mentioned above, in connection with the description of the compounds of the formula (I), as being preferred or as being particularly preferred for A, $R^1$ and $R^2$; Z preferably represents fluorine, chlorine, bromine, $C_1$–$C_4$-alkoxy or phenoxy, in particular, chlorine, methoxy, ethoxy or phenoxy.

The starting materials of the formula (IV) are known and/or can be prepared by processes known per se (cf. U.S. Pat. No. 4,690,707, DE 19 501 174).

The formula (V) provides a general definition of the thiophene derivatives further to be used as starting materials in the process (b) according to the invention. In the formula (V), Q, $R^4$ and $R^5$ each preferably or in particular have those meanings which have already been mentioned above, in connection with the description of the compounds of the formula (I), as being preferred or as being particularly preferred for Q, $R^4$ and $R^5$.

The starting materials of the formula (V) are known and/or can be prepared by processes known per se (cf. EP 30 142/U.S. Pat. No. 4,481,029/U.S. Pat. No. 4,599,103/U.S. Pat. No. 4,701,535, Preparation Examples).

The formula (VI) provides a general definition of the substituted thiophene derivatives to be used as starting materials in the process (c) according to the invention for preparing the compounds of the formula (I). In the formula (VI), Q, $R^4$ and $R^5$ each preferably or in particular have those meanings which have already been mentioned above, in connection with the description of the compounds of the formula (I), as being preferred or as being particularly preferred for Q, $R^4$ and $R^5$; Z preferably represents fluorine, chlorine, bromine, $C_1$–$C_4$-alkoxy or phenoxy, in particular chlorine, methoxy, ethoxy or phenoxy.

The starting materials of the formula (VI) are known and/or can be prepared by processes known per se.

The formula (VIII) provides a general definition of the substituted aminothiophenes to be used as starting materials in the process (d) according to the invention for preparing compounds of the general formula (I). In the general formula (VIII), $R^4$ and $R^5$ each preferably or in particular have those meanings which have already been mentioned above, in connection with the description of the compounds of the general formula (I) according to the invention, as being preferred or as being particularly preferred for $R^4$ and $R^5$.

The starting materials of the general formula (VIII) are known and/or can be prepared by processes known per se (cf. Aust. J. Chem. 48 (1995), 1907–1916).

Suitable diluents for carrying out the processes (a), (b), (c) and (d) according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether, ketones, such as acetone, butanone or methyl isobutyl ketone; nitrites, such as acetonitrile, propionitrile or benzonitrile; amides, such as N,N-dimethylformamide, N,N-dimethylacetamide, N-methylformanilide, N-methylpyrrotidone or hexamethylphosphoric triamide; esters, such as methyl acetate or ethyl acetate, and sulphoxides, such as dimethyl sulphoxide.

The processes (a), (b), (c) and (d) according to the invention are preferably carried out in the presence of a suitable reaction auxiliary. Suitable reaction auxiliaries are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the processes (a), (b), (c) and (d) according to the invention, the reaction temperatures can be varied within a relatively wide range. In general, the processes are carried out at temperatures between −20° C. and +150° C., preferably between −10° C. and +120° C.

The processes (a), (b), (c) and (d) according to the invention are generally carried out under atmospheric pressure. However, it is also possible to carry out the processes according to the invention under elevated or reduced pressure—in general between 0.1 bar and 10 bar.

For carrying out the processes (a), (b), (c) and (d) according to the invention, the starting materials are generally employed in approximately equimolar amounts. However, it is also possible to use a relatively large excess of one of the components.

The reaction is generally carried out in a suitable diluent in the presence of a reaction auxiliary, and the reaction mixture is generally stirred at the required temperature for several hours. Work-up is carried out by customary methods (cf. the Preparation Examples).

If appropriate, sa can be prepared from the compounds of the general formula (I) according to the invention. Such salts are obtained in a simple manner by customary methods for forming salts, for example by dissolving or dispersing a compound of the formula (I) in a suitable solvent, such as, for example, methylene chloride, acetone, tert-butyl methyl ether or toluene, and adding a suitable base. The salts can then—if appropriate after prolonged stirring—be isolated by concentration or filtering off with suction.

The active compounds according to the invention can be used as defoliants, desiccants, haulm killers and, especially, as weed killers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Cappella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

The active compounds according to the invention are suitable, depending on the concentration, for the total control of weeds, for example on industrial terrain and railway tracks, and on paths and squares with or without tree plantings. Equally, the active compounds according to the invention can be employed for the control of weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, in lawns, turf and pasture-land, and for the selective control of weeds in annual crops.

The compounds of the formula (I) according to the invention have strong herbicidal activity and a broad activity spectrum when used on the soil and on above-ground parts of plants. To a certain extent, they are also suitable for the selective control of monocotyledonous and dicotyledonous weeds in monocotyledonous and dicotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam formers.

If the extender used is water, it is also possible to employ, for example, organic solvents as auxiliary solvents. Suitable liquid solvents are essentially the following: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For the control of weeds, the active compounds according to the invention, as such or in their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlorotoluron, cinidon(-ethyl), cinmethylin, cinosulfuron, clefoxydim, clethodim, clodinafop-(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron (-methyl), ethofumesate, ethoxyfen, ethoxysulfuron, etobenzanid, fenoxaprop(-P-ethyl), fentrazamide, flamprop (-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-methyl), flurprimidol, flurtamone, fluthiacet(-methyl), fluthiamide, fomesafen, glufosinate(-ammonium), glyphosate(-isopropylammonium), halosafen, haloxyfop-(-ethoxyethyl), haloxyfop(-P-methyl), hexazinone, imazamethabenz-(-methyl), imazamethapyr, imazamox, imazapic, imazapyr, imazaquin, imazamethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quinmerac, quinoclamine, quizalofop (-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples below.

PREPARATION EXAMPLES

Example 1

(Process (b))

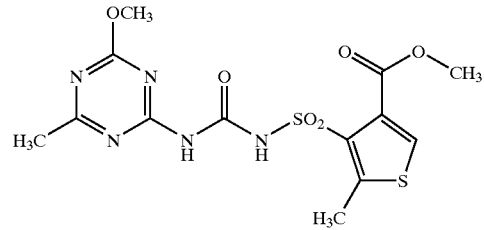

0.75 g (2,9 mmol) of 2-phenoxycarbonylamino-4-methoxy-6-methyl-1,3,5-triazine is dissolved in 40 ml of acetonitrile and admixed successively with 0.75 g (3,2 mmol) of methyl 2-methyl-3-sulphamoyl-thiophene-4-carboxylate and 0.49 g (3.2 mmol) of diazabicycloundecene (DBU). The reaction mixture is stirred at room temperature (about 20° C.) for 12 hours and then concentrated under water-pump vacuum. The residue is taken up in methylene chloride and the mixture is washed with 2N hydrochloric acid and with water, dried with magnesium sulphate and filtered. The filtrate is concentrated under water-pump vacuum, the residue is digested with diethyl ether and the resulting crystalline product is isolated by filtration with suction.

This gives 0.60 g (52% of theory) of N-(4-methoxy-6-methyl-1,3,5-triazin-2-yl)-N'(4-methoxycarbonyl-2-methyl-thien-3-yl-sulphonyl)-urea of melting point 195° C.

Example 2

(Process (d))

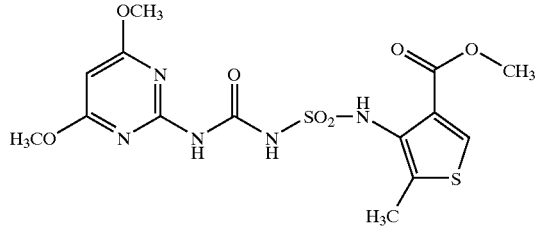

1.05 g (7.5 mmol) of chlorosulphonyl isocyanate are initially charged in 75 ml of methylene chloride. After cooling to −10° C., a solution of 1.16 g (7.5 mmol) of 2-amino-4,6-dimethoxy-pyrimidine in 30 ml of methylene chloride is added dropwise with stirring to this mixture, and the mixture is stirred at −10° C. for 30 minutes. At 0° C., a solution of 1.28 g (7.5 mmol) of methyl 3-amino-2-methyl-thiophene-4-carboxylate and 0.75 g (7.5 mmol) of triethylamine in 50 ml of methylene chloride is then added dropwise, and the reaction mixture is stirred at room temperature (about 20° C.) for 12 hours. 100 ml of water in 100 ml of 2N hydrochloric acid are then added and the organic phase is separated off, washed with 50 ml of water, dried with magnesium sulphate and filtered. The filtrate is concentrated under water-pump vacuum and the residue is crystallized from ethanol.

This gives 2.1 g (66% of theory) of N-(4,6-dimethoxy-pyrimidin-2-yl)-N'-(4-methoxycarbonyl-2-methyl-thien-3-yl-amino-sulphonyl)-urea of melting point 174° C.

Analogously to Examples 1 and 2, and in accordance with the general description of the preparation process according to the invention, it is also possible to prepare, for example, the compounds of the general formula (I) listed in Table 1 below.

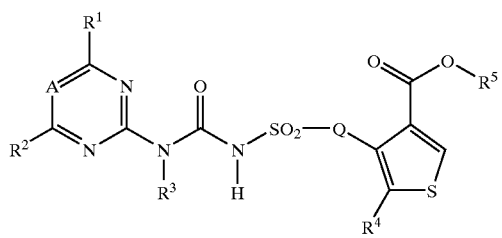

(I)

TABLE 1

Examples of the compounds of the formula (I)

| Ex. No. | A | Q | $R^1$ | $R^2$ | $R^3$ | $R^4$ | $R^5$ | Melting point (° C.) |
|---|---|---|---|---|---|---|---|---|
| 3 | CH | NH | $OCH_3$ | $OCH_3$ | H | $n-C_3H_7$ | $C_2H_5$ | 140 |
| 4 | CH | NH | $OCH_3$ | $OCH_3$ | H | $i-C_3H_7$ | $C_2H_5$ | 154 |
| 5 | CH | NH | $OCH_3$ | $OCH_3$ | H | $C_2H_5$ | $CH_3$ | 195 |
| 6 | CH | — | $OCH_3$ | $OcH_3$ | H | $CH_3$ | $CH_3$ | 194 |

Starting Materials of the Formula (V)

Example V-1)

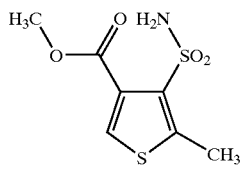

Step 1

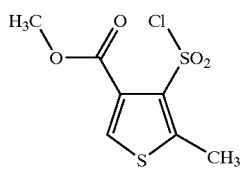

At from 0° C. to 5° C., a solution of 19.9 g (0.29 mol) of sodium nitrite in 60 ml of water is added dropwise with stirring to a solution of 42.7 g (0.25 mol) of methyl 3-amino-2-methyl-thiophene-4-carboxylate in 75 ml of 10% strength aqueous hydrochloric acid. The reaction mixture is stirred at from 0° C. to 5° C. for 60 minutes. The excess of nitrite is subsequently destroyed using amidosulphonic acid. At from 0° C. to 5° C., the mixture is then added dropwise with stirring to a solution of 35 g (0.55 mol) of sulphur dioxide in 300 ml of methylene chloride. After addition of 1.5 g of copper(I) chloride and 1.5 g of dodecyl-trimethylammonium bromide, the reaction mixture is stirred at 40° C. for 60 minutes and then at 20° C. for 12 hours. 18 ml of 35% strength aqueous hydrochloric acid are then added, the mixture is stirred at 20° C. for 4 hours and the phases are then separated. The aqueous phase is re-extracted with methylene chloride and the combined organic phases are washed with water, dried with magnesium sulphate and filtered. The filtrate is concentrated under water-pump vacuum and the residue is crystallized from hexane.

This gives 51.7 g (81% of theory) of 4-methoxycarbonyl-2-methyl-thiophene-3-sulphonyl chloride.

Step 2

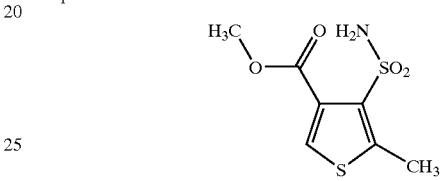

A mixture of 45 g (177 mmol) of 4-methoxycarbonyl-2-methyl-thiophene-3-sulphonyl chloride, 34 g (354 mmol) of ammonium carbonate and 400 ml of methylene chloride is stirred at room temperature (about 20° C.) for 12 hours. The mixture is filtered and the solvent is distilled off from the filtrate under water-pump vacuum, the residue is digested with diethyl ether and the crystalline product is isolated by filtration with suction.

This gives 21.5 g (52% of theory) of 4-methoxycarbonyl-2-methyl-thiophene-3-sulphonamide.

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 litres of water per hectare.

After three weeks, the degree of damage to the plants is rated in % damage in comparison to the development of the untreated control.

The figures denote:

0%=no effect (like untreated control)

100%=total destruction

In this test, for example, the compounds of Preparation Examples 1, 2, 3, 4, 5 and 6 show very strong activity against weeds, and some of them are tolerated well by crop plants, such as, for example, cotton, maize and soya.

TABLE A1

Pre-emergence test/greenhouse

| Active compound of Preparation Example No. | Application rate (g of ai/ha) | Cotton | Alopecurus | Amaranthus | Stellaria | Viola |
|---|---|---|---|---|---|---|
| 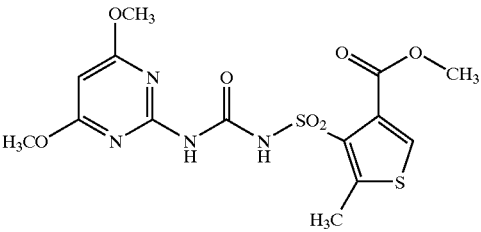 (6) | 15 | 0 | 80 | 90 | 90 | 100 |

TABLE A2

Pre-emergence test/greenhouse

| Active compound of Preparation Example No. | Application rate (g of ai/ha) | Maize | Cyperus | Chenopodium | Matricaria | Viola |
|---|---|---|---|---|---|---|
| 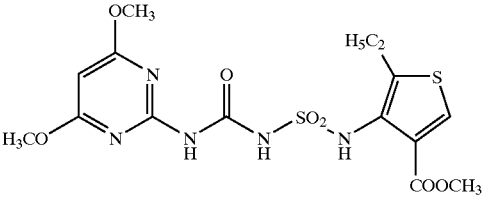 (5) | 125 | 20 | 95 | 95 | 100 | 95 |

TABLE A3

Pre-emergence test/greenhouse

| Active compound of Preparation Example No. | Application rate (g of ai/ha) | Soya | Matricaria | Stellaria | Veronica | Viola |
|---|---|---|---|---|---|---|
| 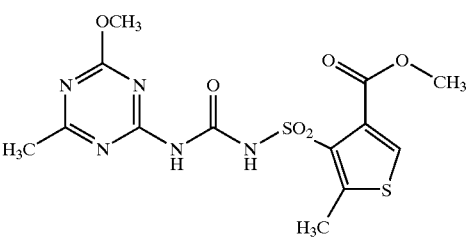 (1) | 4 | 10 | 95 | 95 | 95 | 100 |

TABLE A4

Pre-emergence test/greenhouse

| Active compound of Preparation Example No. | Application rate (g of ai/ha) | Alopecurus | Abutilon | Amaranthus | Sinapis |
|---|---|---|---|---|---|
| 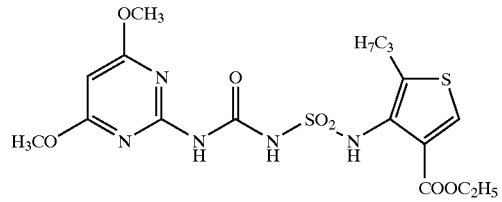 (3) | 250 | 70 | 80 | 90 | 90 |

TABLE A5

Pre-emergence test/greenhouse

| Active compound of Preparation Example No. | Application rate (g of ai/ha) | Alopecurus | Cyperus | Abutilon | Amaranthus | Sinapis |
|---|---|---|---|---|---|---|
| 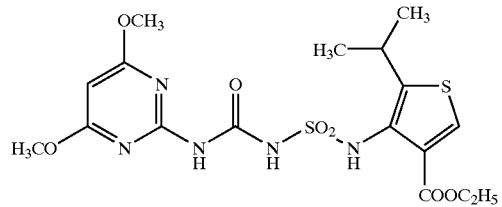 (4) | 250 | 100 | 90 | 95 | 90 | 90 |

TABLE A6

Pre-emergence test/greenhouse

| Active compound of Preparation Example No. | Application rate (g of ai/ha) | Maize | Cyperus | Abutilon | Amaranthus | Sinapis |
|---|---|---|---|---|---|---|
| 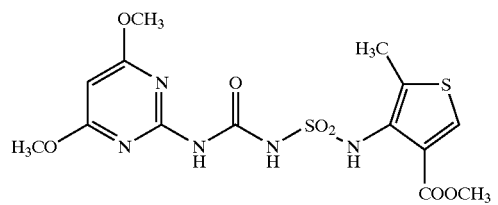 (2) | 250 | 20 | 95 | 90 | 95 | 95 |

Example B

Post-emergence test

Solvent: 5 parts by weight of acetone
Emulsifier: 1 part by weight of alkylaryl polyglycol ether To produce a suitable preparation of active compound, one part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compound desired are applied per unit are. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 1, 2, 5 and 6 exhibit very strong activity against weeds, and some of them are tolerated well by crop plants, such as, for example, barley and wheat.

TABLE B1

Post-emergence test/greenhouse

| Active compound of Preparation Example No. | Application rate (g of ai/ha) | Alopecurus | Echinochloa | Lolium | Abutilon | Stellaria | Veronica | Viola |
|---|---|---|---|---|---|---|---|---|
| (1) | 15 | 100 | 100 | 100 | 100 | 100 | 100 | 100 |

TABLE B2

Post-emergence test/greenhouse

| Active compound of Preparation Example No. | Application rate (g of ai/ha) | Barley | Alopecurus | Abutilon | Amaranthus | Stellaria |
|---|---|---|---|---|---|---|
| (6) | 4 | 20 | 90 | 100 | 100 | 95 |

TABLE B3

Post-emergence test/greenhouse

| Active compound of Preparation Example No. | Application rate (g of ai/ha) | Wheat | Amaranthus | Matricaria | Viola | Xanthium |
|---|---|---|---|---|---|---|
| (2) | 125 | 0 | 100 | 100 | 100 | 95 |

TABLE B4

Post-emergence test/greenhouse

| Active compound of Preparation Example No. | Application rate (g of ai/ha) | Wheat | Setaria | Chenopodium | Ipomoea | Matricaria |
|---|---|---|---|---|---|---|
|  (5) | 125 | 20 | 90 | 100 | 100 | 100 |

What is claimed is:

1. A compound of the Formula (I)

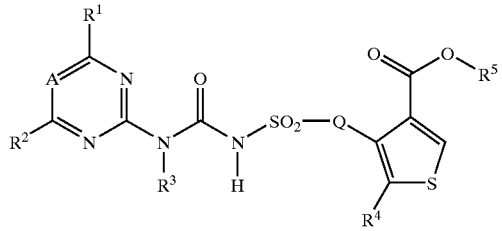

wherein

A represents nitrogen,

Q represents a single bond or represents NH, $R^1$ represents hydrogen, represents halogen, represents in each case optionally cyano-, halogen- or $C_1$–$C_4$-alkoxy-substituted alkyl, alkoxy, alkylthio, alkylamino or dialkylamino having in each case 1 to 4 carbon atoms in the alkyl groups, or represents in each case optionally cyano-, halogen-, $C_1$–$C_4$-alkyl- or $C_1$–$C_4$-alkoxy-substituted phenoxy, oxetanyloxy, furyloxy or tetrahydrofuryloxy, $R^2$ represents hydrogen, represents halogen, represents in each case optionally cyano-, halogen- or $C_1$–$C_4$-alkoxy-substituted alkyl, alkoxy, alkylthio, alkylamino or dialkylamino having in each case 1 to 4 carbon atoms in the alkyl groups, represents in each case optionally cyano-, halogen-, $C_1$–$C_4$-alkyl- or $C_1$–$C_4$-alkoxy-substituted phenoxy, oxetanyloxy, furyloxy or tetrahydrofuryloxy, $R^3$ represents hydrogen or represents optionally $C_1$–$C_4$-alkoxy-, $C_1$–$C_4$-alkyl-carbonyl- or $C_1$–$C_4$-alkoxy-carbonyl-substituted alkyl having 1 to 4 carbon atoms, $R^4$ represents optionally cyano-, halogen- or $C_1$–$C_4$-alkoxy-substituted alkyl having 1 to 6 carbon atoms and—if Q represents NH— also represents hydroagen, and $R^5$ represents hydrogen, represents optionally cyano-, halogen- or $C_1$–$C_4$-alkoxy-substituted alkyl having 1 to 6 carbon atoms, represents in each case optionally halogen-substituted alkenyl or alkinyl having in each case 2 to 6 carbon atoms, represents in each case optionally cyano-, halogen- or $C_1$–$C_4$-alkyl-substituted cycloalkyl or cycoalkylalkyl having in each case 3 to 6 carbon atoms in the cycloalkyl groups and optionally 1 to 4 carbon atoms in the alkyl moiety, or represents in each case optionally cyano-, halogen-, $C_1$–$C_4$-alkyl- or $C_1$–$C_4$-alkoxy-substituted oxetanyl, furyl or tetrahydrofuryl and a salt of the compound of the Formula (I).

2. The compound according to claim 1, wherein $R^1$ represents hydrogen, fluorine, chlorine, bromine, iodine, or represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^2$ represents fluorine, chlorine, bromine, or represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^3$ represents hydrogen or represents in each case optionally methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl or ethyl, $R^4$ represents in each case optionally cyano-, fluorine-, chlorine-, methoxy- or ethoxy-substituted methyl, ethyl, n- or i-propyl, n-, i-, s- or t-butyl, and $R^5$ represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, represents in each case optionally fluorine-, chlorine- or bromine-substituted propenyl, butenyl, propinyl or butinyl, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl.

3. The compound according to claim 1, wherein $R^1$ represents hydrogen, fluorine, chlorine, bromine, represents in each case optionally fluorine-, chlorine-, methoxy- or ethoxy-substituted methyl, ethyl, methoxy, ethoxy, methylthio, ethylthio, methylamino, ethylamino, or represents dimethylamino, $R^2$ represents fluorine, chlorine, bromine, represents in each case optionally fluorine-, chlorine-, methoxy- or ethoxy-substituted methyl, ethyl, methoxy, ethoxy, methylthio, ethylthio, methylamino or ethylamino, or represents dimethylamino, $R^3$ represents hydrogen or methyl, $R^4$ represents in each case optionally fluorine- or chlorine-substituted methyl, ethyl, n- or i-propyl, and $R^5$ represents in each case optionally fluorine-, chlorine-, methoxy- or ethoxy-substituted methyl, ethyl, n- or i-propyl, or represents in each case optionally fluorine- or chlorine-substituted propenyl or propinyl.

4. The compound of claim 1, wherein said compound is a salt of said compound of the Formula I and said salt is selected from the group consisting of a sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salt of said compound according to claim 1.

5. A process for preparing a compound according to claim 1 comprising:

reacting a substituted aminoazine of the Formula (IV)

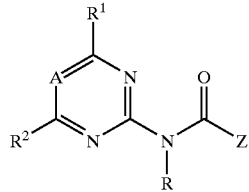

(IV)

wherein

A, $R^1$ and $R^2$ are each as defined in claim 1,

Z represents halogen, alkoxy or aryloxy and

R has the meaning given for $R^3$ in claim 1 or represents the grouping —C(O)—Z, with a thiophene derivative of the Formula (V)

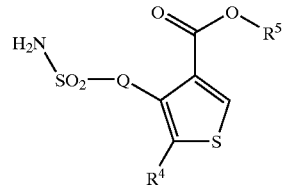

(V)

wherein

Q, $R^4$ and $R^5$ are each as defined in claims 1 to 4, optionally in the presence of a reaction auxiliary and optionally in the presence of a diluent, said process optionally further comprising the step of converting the compound obtained into a salt.

6. An herbicidal composition, comprising a compound according to claim 1 and a member selected from the group consisting of one or more extenders, one or more surfactants and combinations thereof.

7. A method for controlling undesirable vegetation, comprising the step of allowing one or more compounds according to claim 1 to act on a member selected from the group consisting of one or more undesirable plants, a habitat of said undesirable plants, and combinations thereof.

* * * * *